United States Patent [19]

Harris et al.

[11] 4,287,127

[45] Sep. 1, 1981

[54] PRODUCTION OF TETRAHYDROFURAN

[75] Inventors: Norman Harris, Stockton-on-Tees; Alan J. Dennis, Middlesbrough; George E. Harrison, Billericay, all of England

[73] Assignee: Davy McKee (Oil & Chemicals) Limited, London, England

[21] Appl. No.: 139,568

[22] Filed: Apr. 11, 1980

[30] Foreign Application Priority Data

Apr. 11, 1979 [GB] United Kingdom ............... 12852/79

[51] Int. Cl.³ .......................................... C07D 307/08
[52] U.S. Cl. ............................... 260/346.11; 568/670; 568/678
[58] Field of Search ................... 260/346.11; 568/670, 568/678

[56] References Cited

U.S. PATENT DOCUMENTS

| | | | |
|---|---|---|---|
| 3,929,915 | 12/1975 | Cumbo et al. | 260/346.11 X |
| 4,005,112 | 1/1977 | Smith | 260/346.11 |
| 4,064,145 | 12/1977 | Taylor | 260/346.11 |

OTHER PUBLICATIONS

Brown et al., Tetrahedron Letters, No. 22, (1969), pp. 1725 and 1726.
Takeshige et al., Chemical Abstracts, vol. 84, (1976), 30856k.

*Primary Examiner*—Richard Raymond
*Attorney, Agent, or Firm*—Bernard, Rothwell & Brown

[57] ABSTRACT

Tetrahydrofuran is produced by converting allyl alcohol to an allyl t-alkyl or -cycloalkyl ether of the general formula:

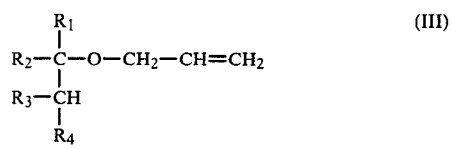

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical, followed by reacting resulting compound of formula (III) under hydroformylation conditions with carbon monoxide and hydrogen in the presence of a hydroformylation catalyst to form a corresponding aldehyde-ether of the general formula:

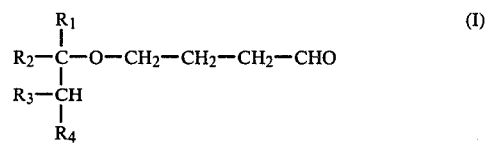

reducing resulting aldehyde-ether of the general formula (I) a corresponding hydroxy-ether of the general formula:

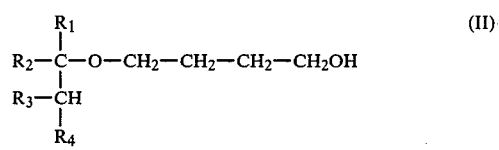

and cleaving resulting hydroxy-ether of the general formula (II) under dehydrating conditions to produce tetrahydrofuran. Typically $R_1$ and $R_2$ each represent a methyl group while $R_3$ and $R_4$ each represent a hydrogen atom. The alkene of the general formula:

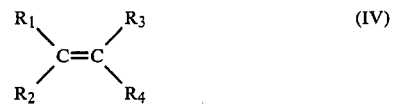

released upon cleavage of the hydroxy-ether of formula (II) can be recycled for reaction with further allyl alcohol to form a further quantity of the ether of the general formula (III).

10 Claims, No Drawings

PRODUCTION OF TETRAHYDROFURAN

This invention relates to the production of tetrahydrofuran.

U.S. Pat. No. 4064145 discloses a process for producing tetrahydrofuran by hydroformylation of allyl alcohol using a rhodium complex catalyst followed by aqueous extraction to recover 4-hydroxybutanal and hydrogenation under acidic conditions.

It is a drawback of this route to tetrahydrofuran, however, that under the hydroformylation conditions employed allyl alcohol, in addition to forming propanol as a by-product as a result of hydrogenation, undergoes isomerization to propionaldehyde. Moreover the hydroformylation of allyl alcohol appears to be complicated by very ready deactivation of the rhodium complex catalyst possibly induced by by-products of the reaction. Additionally, the desired intermediate 4-hydroxybutyraldehyde tends to undergo internal aldolization spontaneously to form 2-hydroxytetrahydrofuran which is somewhat difficult to convert to butane-1,4-diol by ring opening and reduction, before formation of tetrahydrofuran can take place. For all of these reasons the production of tetrahydrofuran by a route involving hydroformylation of allyl alcohol is fraught with difficulties.

Accordingly the present invention seeks to provide a process whereby allyl alcohol may be converted to tetrahydrofuran by a process including a hydroformylation step wherein the risk of deactivation of the catalyst due to the deactivating effect experienced by hydroformylation of allyl alcohol is essentially avoided.

The invention further seeks to provide a process for the production of tetrahydrofuran from allyl alcohol which includes a hydroformylation step but which avoids the use of 2-hydroxytetrahydrofuran as an intermediate product.

According to the present invention there is provided a process for the production of tetrahydrofuran which comprises reducing an aldehyde-ether of the general formula:

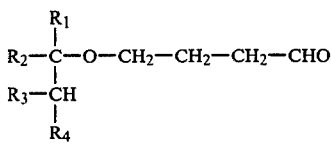

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical to form a hydroxy-ether of the general formula:

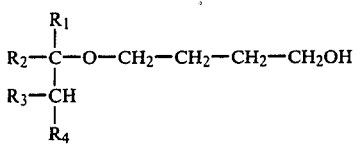

wherein $R_1$, $R_2$, $R_3$ and $R_4$ are as defined above, and cleaving resulting hydroxy-ether of the general formula (II) under dehydrating conditions to produce tetrahydrofuran.

The invention also provides a process for the production of tetrahydrofuran which comprises converting allyl alcohol to an allyl t-alkyl or -cycloalkyl ether of the general formula:

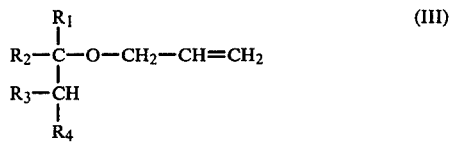

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical, reacting resulting compound of formula (III) under hydroformylation conditions with carbon monoxide and hydrogen in the presence of a hydroformylation catalyst to form an aldehyde-ether of the general formula:

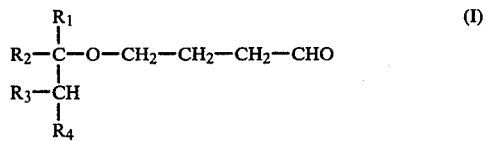

wherein $R_1$, $R_2$, $R_3$ and $R_4$ have the meanings ascribed to them above, reducing resulting aldehyde-ether of the general formula (I) to form a corresponding hydroxy-ether of the general formula:

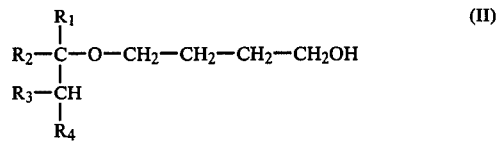

wherein $R_1$, $R_2$, $R_3$ and $R_4$ have the meanings ascribed to them above, and cleaving resulting hydroxy-ether of the general formula (II) under dehydrating conditions to produce tetrahydrofuran.

In the above general formulae (I) to (III) $R_1$ and $R_2$ each preferably represent, independently of the other, a methyl or ethyl group, whilst $R_3$ preferably represents a hydrogen atom or a methyl group and $R_4$ preferably represents a hydrogen atom. In a particularly preferred process $R_1$ and $R_2$ each represent a methyl group and $R_3$ and $R_4$ each represent a hydrogen atom.

The production of aldehyde ethers of the general formula (I) is more fully described in our copending patent application Ser. No. 139,591, filed simultaneously herewith, the disclosure of which is herein incorporated by reference.

Cleavage of the hydroxy-ether of the general formula (II) yields an olefin of the general formula:

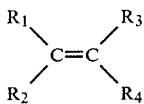   (IV)

wherein $R_1$, $R_2$, $R_3$ and $R_4$ are as defined above. As examples of olefins of the formula (IV) there can be mentioned iso-butylene, 2-methylbut-1-ene, 2-methylbut-2-ene, 2,3-dimethylbut-2-ene, 3-methylpent-2-ene, 2-ethylbut-1-ene, 1-methylcyclohexene and 1-methylcyclopentene.

Etherification of allyl alcohol can be effected by reaction with an olefin of the general formula (IV), conveniently in the presence of an acidic catalyst. The etherification is a reversible reaction and is favoured by the use of low temperatures, for example a temperature in the range of from about 0° C. to about 80° C. Usually it will be preferred to effect etherification of allyl alcohol at about 60° C. or less, preferably in the range of from about 15° C. to about 60° C., for example in the range of from about 35° C. to about 60° C. Since the olefin may be volatile it may be necessary to effect the etherification reaction under elevated pressure. Typical acidic catalysts include ion exchange resins, preferably in anhydrous form, containing sulphonic acid and/or carboxylic acid groups, such as Amberlyst 15 and Dowex 50 resins, as well as aqueous acids, e.g. aqueous solutions of phosphoric acid or dilute aqueous solutions of sulphuric acid (containing, for example, 10% w/v sulphuric acid or less), acid zeolites, acid clays, and organic acids such as p-toluenesulphonic acid or formic acid.

Since a preferred method of converting allyl alcohol to an allyl t-alkyl or -cycloalkyl ether of the general formula (III) comprises reaction of allyl alcohol with an olefin of the general formula (IV) in the presence of an acidic catalyst, the olefin of formula (IV) released upon cleavage of the hydroxy-ether of the general formula (II) can be recycled to the allyl t-alkyl or -cycloalkyl ether formation step.

In the cleavage of the hydroxy-ether of the general formula (II) there may be formed as by-product a tertiary alcohol of the general formula:

$$\begin{array}{c} R_1 \\ | \\ R_2-C-OH \\ | \\ R_3-CH \\ | \\ R_4 \end{array}$$   (V)

wherein $R_1$, $R_2$, $R_3$ and $R_4$ are as defined above. Such an alcohol of the general formula (V) may be dehydrated in the presence of an acidic catalyst to form a corresponding olefin of the general formula (IV) which can be recycled for use in formation of the allyl t-alkyl or -cycloalkyl ether of the general formula (III).

Cleavage of the hydroxy-ether of the general formula (II) can be effected in the presence of a suitable acidic catalyst. As examples of acidic catalysts for use in ether formation and cleavage there can be mentioned aqueous acids, such as aqueous phosphoric acid or sulphuric acid, as well as acidic ion exchange resins, acidic clays, acidic alumina, acidic alumino-silicates and silica.

Cleavage of the hydroxy-ether of the general formula (II) is effected under dehydrating conditions. Such conditions may comprise, for example, contact of the hydroxy ether of the general formula (II) with an acidic catalyst at a temperature and for a time sufficient to effect dehydration and cyclisation. The invention thus contemplates the use of long contact times of the hydroxy ether of the general formula (II) with the acidic catalyst and/or elevated temperatures, more particularly temperatures in excess of 100° C., e.g. up to about 160° C. or more, for example up to about 180° C. Cleavage of the hydroxy-ether of the general formula (II) can also give rise to the formation of butane-1,4-diol, particularly under relatively mild conditions. Although butane-1,4-diol is in many instances a valuable by-product of the cleavage step, it will often be preferred to select conditions conducive to driving the dehydration-cyclisation reaction as far as possible towards completion in the cleavage step. If not required as a product, any butane-1,4-diol formed in the cleavage step can be recycled to the cleavage step for dehydration and cyclisation to tetrahydrofuran. The catalyst and conditions required to produce an acceptable tetrahydrofuran:butane-1,4-diol product ratio in the cleavage step can readily be determined by a process of "self-directing optimization" (see Technometrics, November 1962).

In the cleavage step there may be formed as a by-product a diether of the general formula:

$$R'-O-CH_2-CH_2-CH_2-O-R'$$   (VI)

wherein R' represents a radical of the general formula $$\begin{array}{c} R_1 \\ | \\ R_2-C- \\ | \\ R_3-CH \\ | \\ R_4 \end{array}$$

wherein $R_1$, $R_2$, $R_3$ and $R_4$ are as defined above. This can be recycled with advantage to the cleavage step to undergo cleavage itself to form further hydroxy-ether of the general formula (II) and/or tetrahydrofuran and olefin of the general formula (IV).

Recovery of product tetrahydrofuran can be effected in any convenient manner. For example, if cleavage of the hydroxy ether of the general formula (II) is conducted using an acidic ion exchange resin, distillation of the reaction product mixture or water washing can be used. On the other hand, when using an aqueous acid for ether cleavage, the aqueous layer will contain much of the tetrahydrofuran; this can be recovered by neutralization and subsequent distillation.

Reduction of the aldehyde ether of the general formula (I) to the hydroxy-ether of the general formula (II) can be effected in any suitable manner, for example, by catalytic hydrogenation under atmospheric, sub-atmospheric or super-atmospheric pressure. Reduction is preferably effected under conditions which are not conductive to ether cleavage. Thus it is preferred to avoid acidic conditions in the reduction step. Raney nickel is a suitable hydrogenation catalyst. Hydrogenation can be effected at ambient, sub-ambient or elevated temperature, e.g. at a temperature in the range of from about 150° C. up to about 120° C. or higher, e.g. up to about 180° C. Other hydrogenation catalysts include commercially available supported metal hydrogenation catalysts, as well as copper chromite and palladium hydrogenation catalysts. Reduction by means of sodium borohydride or lithium aluminum hydride is also feasible.

When using a solid catalyst, such as nickel or other metal on a granular support, a trickle bed system can be used for passing the hydrogen and aldehyde-ether of the formula (I) over the catalyst.

As examples of hydrogenation catalysts there can be mentioned $PtO_2$, Pd/C, $Pt/Al_2O_3$ and commercial catalysts such as Girdler G69 catalyst. Pressures of up to 15 kg/cm² absolute or higher can be used.

In the hydroformylation step, the hydroformylation catalyst may be any Group VIII metal-containing hydroformylation catalyst known to be effective for catalysing the hydroformylation of terminal olefins. Preferably the catalyst is a rhodium-containing catalyst comprising rhodium in complex combination with carbon monoxide and a triorganophosphine ligand, such as triphenylphosphine. When using such a catalyst the concentration of rhodium in the reaction medium may range from about 5 parts per million by weight up to about 1000 parts per million of rhodium or more, calculated as rhodium metal. Typically the rhodium concentration ranges from about 20 parts per million up to about 400 parts per million, e.g. about 40 to about 300 parts per million, calculated as rhodium metal. The reaction medium may contain excess triorganophosphine, e.g. about 2 moles up to about 100 moles or more of excess free triorganophosphine per gram atom of rhodium. Usually the hydrogen:carbon monoxide molar ratio is approximately 1:1, e.g. about 1.05:1. The hydroformylation conditions typically include use of reaction temperatures of from about 20° C. up to about 160° C., e.g. about 70° C. to about 120° C. and use of a partial pressure of hydrogen of from about 0.1 kg/cm² absolute up to about 10 kg/cm² absolute or more and a partial pressure of carbon monoxide of about 0.1 kg/cm² absolute up to about 10 kg/cm² absolute or more. The overall pressure may be about 2 kg/cm² or less. The reaction can be effected in the presence of a solvent, e.g. a mixture of aldehyde condensation products such as is disclosed in British Pat. No. 1338237, or in the absence of added solvent. The aldehyde-ether of the general formula (I) can be recovered from the hydroformylation reaction medium by conventional methods, e.g. distillation.

In the hydroformylation step a by-product is the corresponding iso-aldehyde ether of the general formula:

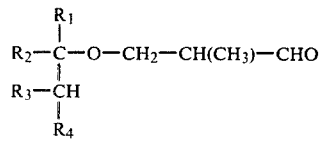

wherein $R_1$, $R_2$, $R_3$ and $R_4$ are as defined above. It may not be necessary to separate this from the aldehyde-ether of the general formula (I) prior to the reduction step, nor to separate the corresponding reduction product, i.e. the iso-hydroxy-ether of the general formula:

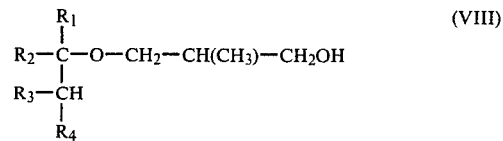

wherein $R_1$, $R_2$, $R_3$ and $R_4$ are as defined above, from the hydroxy-ether of the general formula (II), prior to the cleavage step. In this case a by-product of the cleavage step is 2-methylpropane-1,3-diol. Another by-product of the cleavage step may be the corresponding diether of the general formula:

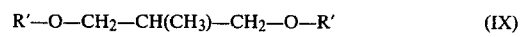

wherein R' represents a radical of the formula:

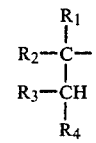

wherein $R_1$, $R_2$, $R_3$ and $R_4$ are as defined above. Hence, if no intermediate purification is effect, the cleavage step may yield a complex reaction mixture containing olefin of the general formula (IV), tertiary alcohol of the general formula (V), tetrahydrofuran, unreacted hydroxy-ether of the general formula (II), iso-hydroxy-ether of the general formula (VIII), diethers of the general formulae (VII) and (IX), butane-1,4-diol, 2-methylpropane-1,3-diol, and small amounts of minor by-products, such as complex aldehyde condensation products, (derived from the compounds of the general formulae (I) and (VII)), of the type described in British Pat. No. 1338237.

The hydroxy-ethers of the general formulae (II) and (VIII) and the diol-ethers of the general formulae (VI) and (IX) in this mixture can with advantage be recycled to the cleavage step since they can undergo cleavage in a further pass into contact with the acidic catalyst to liberate olefin of the general formula (IV). The complex reaction mixture from the cleavage step can be separated, for example, by distillation into several fractions, possibly in several stages (of which at least one stage may be maintained under reduced pressure). Thus when $R_1$ and $R_2$ each represent methyl and $R_3$ and $R_4$ each represent a hydrogen atom, a series of five distillation stages can be used, for example, in order to separate components of the crude reaction mixture from the cleavage step. In the first stage of the series iso-butylene is recovered overhead; a mixture of low boiling products including t-butanol and tetrahydrofuran, is taken overhead from a second column of the series. Tetrahydrofuran can be recovered from this mixture by re-distillation. A mixture of hydroxy-ethers of the general formulae (II) and (VIII) and of diol ethers of the general formulae (VII) and (IX) forms an overhead product from a third column which is maintained under vacuum. This mixture can be recycled to the cleavage step. 2-methyl-propane-1,3-diol is removed overhead in a further column (also under vacuum), whilst butane-1,4-diol is recovered overhead in a fifth, vacuum distillation stage of the series; the bottoms products from this fifth column comprises heavy ends, e.g. complex aldehyde condensation products, which can be burnt as a fuel.

The invention is further illustrated by reference to the following Examples.

EXAMPLE 1

A. Preparation of allyl t-butyl ether.

50 ml allyl alcohol and 5 g dry Amberlyst 15 resin were placed in a 300 ml capacity autoclave agitated by means of a Magnedrive unit actuating an induction stirrer. (The word "Amberlyst" is a Registered Trade Mark). The autoclave was purged with iso-butylene and then warmed to 30° C. in an oil bath and pressurised to 1.75 kg/cm$^2$ absolute with iso-butylene. The pressure dropped as reaction took place and further iso-butylene was introduced to raise the pressure once again to 1.75 kg/cm$^2$. This procedure was repeated as necessary until reaction was complete after approximately 90 minutes as indicated by the cessation of uptake of iso-butylene. After releasing the pressure the product was decanted from the resin and washed several times with deionised water. The crude product was subjected to a partial vacuum to remove iso-butylene (until gas chromatography showed that there was less than 0.1% iso-butylene in the product) and then dried over anhydrous sodium carbonate. Gas chromatography, using a gas chromatograph with a flame ionisation detector and temperature programming, indicated that allyl t-butyl ether had been formed with greater than 98% efficiency. The chromatographic column was 1.83 m × 3.2 mm O.D. stainless steel, packed with 10% by weight diethylene glycol succinate on Chromosorb W.

B. Hydroformylation of allyl t-butyl ether

The same autoclave was charged with the calculated quantities of HRh(CO)(PPh$_3$)$_3$ and PPh$_3$ and then sufficient Filmer 351 was added to bring the volume of liquid to 90 ml. (Filmer 351 is a complex mixture of polymeric condensation products of n- and iso-butyraldehydes of the type disclosed in British Pat. No. 1338237). The autoclave was then sealed. The body of the autoclave was immersed in an oil bath capable of being heated and thermostatically controlled to ±1° C. between 40° C. and 180° C. by means of a heater/stirrer. The pressure within the reactor could be monitored by means of a pressure transducer linked to a single pen recorder. The stirrer was switched on and its speed adjusted to 500 r.p.m. The reactor was purged with a hydrogen/carbon monoxide gas mixture, the composition of which depended on the planned H$_2$:CO ratio. The reactor was then pressurised to a level which was 0.35 kg/cm$^2$ below the desired operating pressure and isolated. The stirrer speed was then adjusted to 2000 r.p.m. and the temperature increased to the desired value. The pressure was then increased to the required level using the same H$_2$/CO mixture and the reactor isolated once more. Subsequently 10 ml of allyl t-butyl ether were pumped into the reactor, whereupon reaction commenced. The rate of reaction was monitored by timing the pressure drop between two defined levels ±0.07 kg/cm$^2$ around the design pressure. When the pressure reached the lower defined level, the reactor was repressurised to a level 0.14 kg/cm$^2$ above the design operating pressure with an approximately 1:1 H$_2$:CO mixture as demanded by the stoichiometric requirements of the reaction and the procedure repeated until the reaction was complete, at which time the rate of pressure drop was negligible. The oil heater/stirrer was then switched off, the hot oil run out of the bath and replaced with cold oil. The oil stirrer was switched on again and the reactor cooled to 40° C. The reactor stirrer was then switched off and the reactor depressurised and opened to permit the reaction solution to be removed for analysis and/or storage.

Analysis of the reaction solution was effected utilising the gas chromatographic method outlined above in Section A. With the aid of an integrator peak areas were computed and from these results molar selectivities were calculated using response factors determined from pure compounds isolated from the reaction solution by preparative chromatography.

The results are set out in the Table.

TABLE

| Run No. | Temp. °C. | Partial Pressure kg/cm$^2$ CO | Partial Pressure kg/cm$^2$ H$_2$ | Rh conc. ppm | TPP conc. wt. % | Reaction Products (yield %) PTBE | Unknown | trans-P(=)TBE | ATBE | cis-P(=)TBE | TBMPA | TBBA |
|---|---|---|---|---|---|---|---|---|---|---|---|---|
| 1 | 70 | 0.53 | 0.53 | 200 | 40 | 0.45 | 0.01 | 3.91 | 2.88 | 1.10 | 11.11 | 80.54 |
| 2 | 50 | 0.53 | 0.53 | 1000 | 10 | 0.73 | 0.41 | 4.87 | — | 0.84 | 17.62 | 75.53 |
| 3 | 100 | 0.53 | 0.53 | 200 | 10 | 1.27 | 0.17 | 29.72 | — | 7.43 | 8.75 | 52.66 |
| 4 | 70 | 3.79 | 3.79 | 50 | 10 | 0.86 | 0.28 | 1.05 | 1.43 | 0.35 | 28.61 | 67.42 |
| 5 | 70 | 0.53 | 0.53 | 300 | 20 | 0.74 | 0.33 | 8.57 | trace | 1.93 | 10.16 | 78.27 |
| 6 | 80 | 2.35 | 0.95 | 100 | 20 | 0.59 | 0.19 | 1.71 | 1.32 | 0.68 | 21.87 | 73.64 |

Note:
TPP = triphenylphosphine
PTBE = propyl t-butyl ether
trans-P(=)TBE = trans-propen-1-yl t-butyl ether
ATBE = allyl t-butyl ether
cis-P(=)TBE = cis-propen-1-yl t-butyl ether
TBMPA = 3-t-butoxy-2-methylpropionaldehyde
TBBA = 4-t-butoxy butyraldehyde The reaction residues from these and other experiments were combined and subjected to distillation. 4-t-butoxybutyraldehyde was obtained as a colourless liquid.

C. Reduction of 4-t-butoxybutyraldehyde 25 ml 4-t-butoxybutyraldehyde and 2 gms Raney nickel were introduced into a 300 ml stainless steel bomb fitted with a stirrer, which was then sealed, purged first with nitrogen and then with hydrogen, and pressurised with hydrogen to 17.86 kg/cm$^2$ absolute. The bomb was then heated to 75° C. and maintained at this temperature. The reactant aldehyde hydrogenated smoothly and virtually quantitatively to 4-t-butoxybutanol. At the completion of the reaction, the bomb was cooled and depressurised and the reaction solution was filtered and analysed using the gas chromatographic technique described above in Section A. The peak ascribed to the starting aldehyde had virtually disappeared and a new peak appeared. The identity of this compound as 4-t-butoxy-butan-1-ol was confirmed by ether cleavage under dehydrating conditions to form tetrahydrofuran as described below in Section D.

D. Preparation of tetrahydrofuran 10 ml of 4-t-butoxybutanol, prepared as described in Section C above, and 1 gm dry Amberlyst 15 acid ion exchange resin were placed in a 100 ml round-bottomed flask provided with a magnetic stirrer and a fractionating column and condenser arranged for product distillation. The flask was heated to 120° C. for 4 hours by means of an oil bath. Gas was evolved and a light distillate was collected boiling initially at 64° C. The boiling point subsequently rose to 98° C. towards the end of the reaction. The gas evolved was analysed by gas chromatography using a column containing 20% by weight diethyl succinate on Celite and was identified as iso-butylene. 5.4 gms of distillate were collected, the major organic constituents of which were identified as t-butanol and tetrahydrofuran by means of the gas chromatographic technique discussed above in Section A. The residue in the flask weighed 0.5 gms. The distillate was subsequently re-bulked with the residue and re-analysed. The results are given below:

|  | Distillate | Re-bulked |
|---|---|---|
| Iso-butylene | 4.2% | 2.7% |
| Tetrahydrofuran | 80.7% | 79.5% |
| t-butanol | 14.4% | 15.7% |
| 4-t-butoxybutan-1-ol | 0.1% | 1.1% |
| 1,4-butanediol | 0.1% | 0.1% |
| Others | 0.7% | 0.9% |

EXAMPLE 2

A. Hydroformylation of allyl t-butyl ether 0.10 gms rhodium hydridocarbonyl tris-(triphenylphosphine), i.e. $RhH(CO)(PPh_3)_3$, 90 ml allyl t-butyl ether and 10.0 gms triphenylphosphine were charged to a 300 ml autoclave fitted with a magnetically coupled stirrer, a gas inlet dip tube and an outlet valve. The autoclave was sealed, purged with nitrogen whilst stirring its contents, and isolated. Stirring was continued whilst the temperature of the autoclaves was raised to 73° C. by immersion in an oil-bath fitted with a thermostatically-controlled heater-stirrer. The autoclave was then purged with a 1:1 molar $H_2$:CO mixture and pressurised to 2.1 kg/cm² absolute by closure of the outlet valve. Reaction commenced and proceeded smoothly with a slight exotherm at the beginning of the reaction. As the reaction proceeded, the pressure dropped; when the total pressure reached 1.9 kg/cm² absolute, more 1:1 $H_2$:CO mixture was admitted to the autoclave to restore the pressure to 2.1 kg/cm² absolute. This repressurisation technique was repeated as necessary until no more gas was taken up, indicating that reaction was complete. This took between 3 and 4 hours. The autoclave was cooled, depressurised and opened, and the contents discharged and stored under nitrogen.

The resulting solution was analysed by gas chromatography using helium as carrier gas, a column packed with 10% w/w diethylene glycol succinate on Chromosorb PAW and a flame ionization detector. Selectivities were observed as follows:

5.6% to isomerised/hydrogenated allylic feedstock
18.9% to 3-t-butoxy-2-methyl-propionaldehyde (TBMPA)
75.5% to 4-t-butoxybutyraldehyde (TBBA).

These selectivities are expressed in molar percentages.

The two aldehyde-ethers (TBMPA and TBBA) were separated by distillation from the other constituents of the reaction solution and then purified by distillation and characterised by formation of dimedone derivatives and by measurement of physical data. The following results were obtained:

| Property | TBMPA | TBBA |
|---|---|---|
| Refractive index (at 23° C.) | 1.4128 | 1.4170 |
| Melting point of dimedone derivative | 107–109° C. | 133–135° C. |
| Specific gravity at 25° C. | 0.849 | 0.868 |
| Boiling point |  |  |
| at 743 mm Hg | 151.6° C. | 169.5° C. |
| at 760 mm Hg | 152.3° C. | 170.5° C. |
| at 100 mm Hg | 103.2° C. | 115.6° C. |

Nuclear magnetic resonance spectra were obtained for the compounds as follows, using tetramethyl silane as an internal standard and carbon tetrachloride as solvent:

1. TBBA  $(CH_3)_3C—O—CH_2—CH_2—CH_2—CHO$
        a           b      c      d     e

| Identifying letter of C-atom to which H-atom is attached | Nature of peak | Chemical shift δ relative to TMS |
|---|---|---|
| a | singlet | 1.13 |
| b | triplet | 3.31 |
| c | triplet of triplets | 2.39 |
| d | doublet of triplets | 1.84 |
| e | triplet | 9.62 |

2. TBMPA  $(CH_3)_3C—O—CH_2—CH(CH_3)—CHO$
         a           b       c       d     e

| Identifying letter of C-atom to which H-atom is attached | Nature of peak | Chemical shift δ relative to TMS |
|---|---|---|
| a | singlet | 1.16 |
| b | doublet | 3.56 |
| c | complex multiplet | 2.39 |
| d | doublet | 1.04 |
| e | doublet | 9.66. |

In each case the ratios of the peak areas corresponded to the expected ratios as predicted from the respective assigned structural formula. In the case of the doublets, triplets and multiplets the quoted chemical shift is the centred value.

B. Hydrogenation of t-butoxybutyraldehyde.

25 ml of reaction solution from Part A of this Example and 1.5 gms Raney nickel were charged to a 300 ml stainless steel bomb fitted with a magnetically coupled stirrer and with inlet and outlet gas lines and valves. The bomb was sealed, purged with hydrogen, whilst stirring its contents, and pressurised to 14.1 kg/cm² absolute with hydrogen. The bomb was then heated to 70° C. in an oil bath, the temperature of which could be varied by means of a thermostatically controlled heater-stirrer. The pressure was maintained at 14.1 kg/cm² absolute by admitting further hydrogen as required. The reactor pressure was controlled using a downstream pressure controller and monitored by means of a pressure transducer linked to a recorder. When no further gas was taken up the bomb was cooled and its contents discharged and filtered. Gas chromatographic analysis, using the technique described in Part A of this Example, indicated that virtually quantitative hydrogenation had occurred. The results obtained were as follows:

|  | Reaction Solution from Part A | Hydrogenated Solution |
|---|---|---|
| TBMPA | 18.9 mole % | 0 |
| TBBA | 75.5 mole % | 0 |
| 3-OH MPTBE | 0 | 18.5 mole % |
| 4-OH BTBE | 0 | 74.9 mole % |

Note:
3-OH MPTBE = 3-hydroxy-2-methylpropyl t-butyl ether
4-OH BTBE = 4-hydroxybutyl t-butyl ether.

The structures of 3-OH MPTBE and 4-OH BTBE can be assigned to the hydrogenation products by analysis of the cleavage products produced in Part C hereunder.

C. Production of tetrahydrofuran

A further sample of allyl t-butyl ether was hydroformylated by a method analogous to that described in Part A of this Example and a mixture of TBMPA and TBBA separated by distillation from the reaction mixture. This fraction was then hydrogenated by a method similar to that described in Part B of this Example.

The resulting hydrogenated mixture had the following analysis as determined by gas chromatography:

| 31.05 wt % | 3-OH MPTBE |
|---|---|
| 65.58 wt % | 4-OH BTBE |

8.73 gms of this mixture and 0.4 gms of Amberlyst 15 resin were charged to a 50 ml round bottomed flask provided with a side arm fitted with a septum to facilitate sampling and also provided with a vertical air condenser. The top of the air condenser was fitted with a thermometer and side arm connected to a condenser supplied with coolant at −5° C. and leading to a collection flask with a side arm leading to a Drechsel bottle containing water. The contents of the flask were stirred magnetically and heated to 120° C. on an oil bath. Refluxing commenced and in due course distillate collected in the collection flask. Gas was evolved and was identified as iso-butylene by gas chromatography. After 16 hours the flask was cooled and the distillate weighed and analysed by gas chromatography. The distillate amounted to 2.89 gms and was shown to contain tetrahydrofuran, iso-butylene and t-butanol, of which 81.8% w/w was tetrahydrofuran, corresponding to a yield of 83.6% based upon the 4-OH BTBE in the starting material.

EXAMPLE 3

A. Preparation of allyl 2-methylbut-2-yl ether.

100 gms 2-methylbut-2-ene, 300 gms allyl alcohol and 10 gms Amberlyst 15 resin were charged to a 1-liter flat-bottomed flask containing a magnetic follower and fitted with a stopper incorporating a gas inlet tube dipping below the surface of the liquid in the flask and with an exit tube leading from the gas space to a Drechsel bottle filled with water. The flask was purged with nitrogen and then placed in a water bath at 30° C. on a magnetic stirrer. The contents of the flask were maintained at this temperature for 16 hours and then filtered. After washing 5 times with deionised water, each time at an approximately 1:1 ratio by volume, in order to remove the bulk of the unreacted allyl alcohol, the resulting organic layer was dried over anhydrous sodium carbonate and the ether was purified by distillation. The yield was 137 gms (74.9% based on the olefin), b.p. 125°–127° C. at 770 mm Hg.

B. Hydroformylation of allyl 2-methylbut-2-yl ether.

When 90 ml of allyl 2-methylbut-2-yl ether was used as feedstock, in place of allyl t-butyl ether, in the hydroformylation procedure of Example 2, the following selectivities (expressed in molar percentages) were observed:

7.4% to isomerised/hydrogenated allylic feedstock
19.4% to 3-(2'-methylbutan-2'-oxy)-2-methylpropionaldehyde (MBMPA)
73.2% to 4-(2'-methylbutan-2'-oxy)-butyraldehyde.(MBBA)

C. Hydrogenation of 4-(2'-methylbutan-2'-oxy)-butyraldehyde.

Using as starting material 25 ml of the reaction solution obtained in Part B of this Example in the procedure of Part B of Example 2 the following selectivities were obtained:

|  | Starting Material | Product |
|---|---|---|
| 3-(2'methylbutan-2'-oxy)-2-methyl-propionaldehyde | 19.4 mole % | 0 |
| 4-(2'-methylbutan-2'-oxy)-butyraldehyde | 73.2 mole % | 0 |
| 3-(2'-methylbutan-2'-oxy)-2-methyl-propanol | 0 | 17.4 mole % |
| 4-(2'-methylbutan-2'-oxy)-butanol | 0 | 72.4 mole % |

D. Production of tetrahydrofuran.

Analysis by gas chromatography of the crude hydrogenated mixture from Part C indicated the following composition:

| 3-(2'-methylbutan-2'-oxy)-2-methyl-propanol | 16.25 wt % |
|---|---|
| 4-(2'-methylbutan-2'-oxy)-butanol (4-MBOB) | 67.6 wt % |

Following the technique described in Part C of Example 2, but using 8.29 gms of the above crude hydrogenated mixture as starting material, the concentration of tetrahydrofuran in the distillate, which weighed 5.27 gms, was 39.2% w/w, corresponding to a yield of 81.8% based on the 4-MBOB in the starting material. Besides tetrahydrofuran the major product in the distillate was 2-methylbut-2-ene.

EXAMPLE 4

A Preparation of allyl 2,3-dimethylbut-2-yl ether

The procedure of Part A of Example 3 was repeated utilising 100 gms of 2,3-dimethylbut-2-ene in place of the 100 grms of 2-methylbut-2-ene. This resulted in a yield of 88 gms of allyl 2,3-dimethylbut-2-yl ether (52.1% based on the olefin), b.p. 144°–147° C. at 765 mm Hg.

B. Hydroformylation of allyl 2,3-dimethylbut-2-yl ether

The hydroformylation procedure of Example 2 was repeated utilising 90 ml of allyl 2,3-dimethylbut-2-yl ether in place of allyl t-butyl ether. The selectivities achieved (expressed in molar percentages) were as follows:

6.0% to isomerised/hydrogenated allylic feedstock
19.3% to 3-(2',3'-dimethylbutan-2'-oxy)-2-methylpropionaldehyde 74.7% to 4-(2',3'-dimethylbutan-2'-oxy)-butyraldehyde.

C. Hydrogenation of 4-(2',3'-dimethylbutan-2'-oxy)-butyraldehyde.

Using as starting material in the procedure of Part B of Example 2 25 ml of the reaction solution obtained in Part B of this Example the following selectivities were obtained:

|  | Starting Material | Product |
| --- | --- | --- |
| 3-(2'-dimethylbutan-2'-oxy)-2-methyl-propionaldehyde | 19.3 mole % | 0 |
| 4-(2',3'-dimethylbutan-2'-oxy)-butyraldehyde | 74.7 mole % | 0 |
| 3-(2',3'-dimethylbutan-2'-oxy)-2-methyl-propanol | 0 | 17.2 mole % |
| 4-(2',3'-dimethylbutan-2'-oxy)-butanol | 0 | 72.4 mole % |

D. Production of tetrahydrofuran.

Analysis by gas chromatography of the crude hydrogenated mixture from Part C indicated the following composition:

| 3-(2',3'-dimethylbutan-2'-oxy)-2-methyl-propanol | 15.5 wt % |
| --- | --- |
| 4-(2',3'-dimethylbutan-2'-oxy)-butanol (4-DiMBOB) | 65.1 wt % |

Following the technique described in Part C of Example 2, but using 8.86 gms of the above hydrogenated mixture as starting material, the concentration of tetrahydrofuran in the distillate, which weighed 6.22 gms, was 33.5% w/w, corresponding to a yield of 87.2% based on the 4-DiMBOB in the starting material. Besides tetrahydrofuran the major product in the distillate was 2,3-dimethylbut-2-ene.

EXAMPLE 5

A. Preparation of allyl 1-methylcyclohexyl ether

The procedure of Part A of Example 3 was repeated using 100 gms of 1-methylcyclohexene as the olefin in place of iso-butylene. The yield of allyl 1-methylcyclohexyl ether was 93.5 gms (58.3% based on the olefin), b.p. 138°–140° C. at 240 mm Hg.

B. Hydroformylation of allyl 1-methylcyclohexyl ether

When 90 ml of allyl 1-methylcyclohexyl ether was utilised as feedstock in the hydroformylation procedure of Example 2 the selectivites (expressed in molar percentages) were as follows:

8.0% to isomerised/hydrogenated allylic feedstock
19.0% to 3-(1'-methylcyclohexanoxy)-2-methylpropionaldehyde
73.0% 4-(1'-methylcyclohexanoxy)-butyraldehyde.

C. Hydrogenation of 4-(1'-methylcyclohexanoxy)-butyraldehyde.

Using as starting material in the procedure of Part B of Example 2 25 ml of the reaction solution obtained in Part B of this Example the following results were obtained:

|  | Starting Material | Product |
| --- | --- | --- |
| 3-(1'-methylcyclohexanoxy)-2-methyl-propionaldehyde | 19.0 mole % | 0 |
| 4-(1'-methylcyclohexanoxy)-butyraldehyde | 73.0 mole % | 0 |
| 3-(1'-methylcyclohexanoxy)-2-methyl-propanol | 0 | 19.7 mole % |
| 4-(1'-methylcyclohexanoxy)-butanol (4-MCHB) | 0 | 73.0 mole % |

D. Production of Tetrahydrofuran

Analysis by gas chromatography of the crude hydrogenated mixture from Part C indicated the following composition:

| 3-(1'-methylcyclohexanoxy)-2-methyl-propanol | 17.7 wt % |
| --- | --- |
| 4-(1'-methylcyclohexanoxy)-butanol (4-MCHB) | 65.7 wt % |

Following the technique described in Part C of Example 2, but using 3.16 gms of the above hydrogenated mixture as starting material, the concentration of tetrahydrofuran in the distillate, which weighed 2.335 gms, was 78.8% w/w, corresponding to a yield of 88.7% based on the 4-MCHB in the starting material. Besides tetrahydrofuran, the major product in the distillate was 1-methylcyclohexene.

EXAMPLE 6

100 gms of a mixture of 3-OH MPTBE and 4-OH BTBE were treated by the method described in Part C of Example 2, except that the collection flask was cooled in a "dry ice"/isopropanol trap. The iso-butylene thus collected was used to make a further amount of allyl t-butyl ether which was then purified and successfully hydroformylated by the procedure described in Part A of Example 2, thus demonstrating that an olefin of the general formula (IV) formed by cleavage of a hydroxy ether of the general formula (II) can be recycled to the step of forming an allyl ether of the general formula (III).

EXAMPLE 7

The same autoclave as was used in Example 2 was charged with the following components:

| Component | Amount |
| --- | --- |
| HRh(CO)(PPh$_3$)$_3$ | 0.1 gms |
| PPh$_3$ | 10 gms |
| Allyl t-butyl ether | 90 ml |

Using the procedure described in Section A of Example 2, the course of the reaction was monitored at 73° C. using a 1:1 H$_2$:CO mixture at a total pressure of 4.22 kg/cm$^2$ absolute. Analysis of the reaction solution when gas uptake ceased indicated that substantially all of the allyl t-butyl ether had reacted.

In contrast, on replacing the 90 ml of allyl t-butyl ether with 90 ml of allyl alcohol, the reaction proceeded to only 36% conversion before gas uptake effectively ceased indicating that essentially total deactivation of the catalyst had occurred.

We claim:

1. A process for the production of tetrahydrofuran which comprises reducing an aldehyde-ether of the general formula:

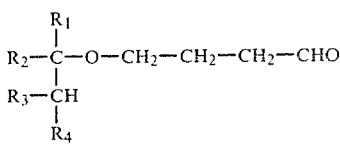 (I)

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical to form a hydroxy ether of the general formula:

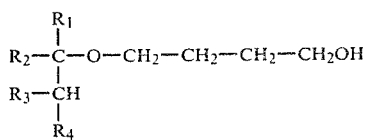 (II)

wherein $R_1$, $R_2$, $R_3$ and $R_4$ are as defined above, cleaving resulting hydroxy-ether of the general formula (II) under dehydrating conditions to produce tetrahydrofuran, and recovering resulting tetrahydrofuran.

2. A process according to claim 1, in which the aldehyde-ether of the general formula (I) is produced by reaction of an allyl t-alkyl or -cycloalkyl ether of the general formula:

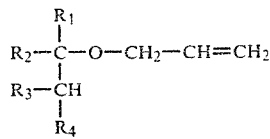 (III)

wherein $R_1$, $R_2$, $R_3$ and $R_4$ have the meanings ascribed to them in claim 1, under hydroformylation conditions with carbon monoxide and hydrogen in the presence of a hydroformylation catalyst.

3. A process according to claim 2, in which the ether of the general formula (III) is produced by reaction of allyl alcohol with an olefin of the general formula:

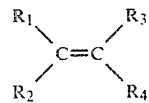 (IV)

wherein $R_1$, $R_2$, $R_3$ and $R_4$ have the meanings ascribed to them in claim 1.

4. A process according to claim 1, in which cleavage of the hydroxy ether of the general formula (II) is effected in the presence of an acidic catalyst.

5. A process according to claim 4, in which the acidic catalyst is selected from aqueous acids, acidic ion exchange resins, acidic clays, acidic alumina, acidic alumino-silicates and silica.

6. A process according to claim 1, in which $R_1$ and $R_2$ each represent, independently of the other, a methyl or ethyl group, $R_3$ represents a hydrogen atom or a methyl group and $R_4$ represents a hydrogen atom.

7. A process for the production of tetrahydrofuran which comprises converting allyl alcohol to an allyl t-alkyl or -cycloalkyl of the general formula:

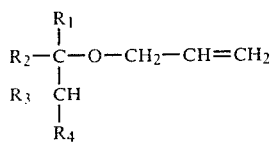 (III)

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical, by reaction with an olefin of the general formula:

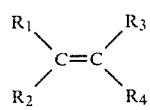 (IV)

wherein $R_1$, $R_2$, $R_3$ and $R_4$ have the meanings ascribed to them above, reacting resulting compound of the general formula (III) under hydroformylation conditions with carbon monoxide and hydrogen in the presence of a hydroformylation catalyst to form an aldehyde-ether of the general formula:

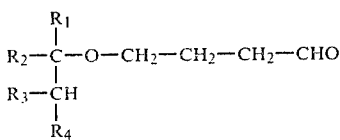 (I)

wherein $R_1$, $R_2$, $R_3$ and $R_4$ have the meanings ascribed to them above, reducing resulting aldehyde ether of the general formula (I) to form a hydroxy-ether of the general formula:

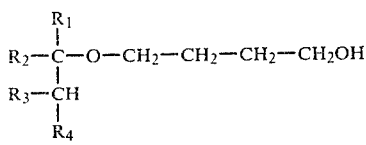 (II)

wherein $R_1$, $R_2$, $R_3$ and $R_4$ have the meanings ascribed to them above, cleaving resulting hydroxy-ether of the general formula (II) under hydrating conditions to produce tetrahydrofuran, and recovering resulting tetrahydrofuran.

8. A process according to claim 7, in which olefin of the general formula (IV) released upon cleavage of the hydroxy-ether of the general formula (II) is recycled for reaction with further allyl alcohol to produce a further quantity of the ether of the general formula (III).

9. A process according to claim 7, in which by-product butane-1,4-diol and/or unreacted hydroxy-ether of the general formula (II) is or are recovered and recycled to the cleavage step.

10. A process according to claim 7, in which diether of the general formula:

$$R'\text{—}O\text{—}CH_2\text{—}CH_2\text{—}CH_2\text{—}CH_2\text{—}O\text{—}R' \quad \text{(VI)}$$
wherein R' represents a radical of the general formula
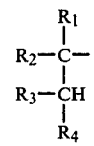
wherein $R_1$, $R_2$, $R_3$ and $R_4$ are as defined in claim 7, formed as by-product in the cleavage of the hydroxyether of the general formula (II) is recycled to the cleavage step.
* * * * *

UNITED STATES PATENT OFFICE
CERTIFICATE OF CORRECTION

Patent No. 4,287,127                Dated September 1, 1981

Inventor(s) Norman Harris, Alan J. Dennis and George E. Harrison

It is certified that error appears in the above-identified patent and that said Letters Patent are hereby corrected as shown below:

Column 4, line 64, "150°C." should read --15°C.--.

Column 5, line 43, "2 kg/cm$^2$" should read --20 kg/cm$^2$--.

Column 13, line 12, "3-(2'-dimethylbutan-2'-oxy)-2-methyl-" should read --3-(2'-3'-dimethylbutan-2'-oxy)-2-methyl- --.

Signed and Sealed this

Twelfth Day of January 1982

[SEAL]

Attest:

GERALD J. MOSSINGHOFF

Attesting Officer    Commissioner of Patents and Trademarks